United States Patent [19]

Woodbridge, III

[11] 4,065,263

[45] * Dec. 27, 1977

[54] ANALYTICAL TEST STRIP APPARATUS

[76] Inventor: Richard G. Woodbridge, III, 40 North Road, Princeton, N.J. 08540

[*] Notice: The portion of the term of this patent subsequent to Feb. 8, 1994, has been disclaimed.

[21] Appl. No.: 696,231

[22] Filed: June 14, 1976

Related U.S. Application Data

[63] Continuation-in-part of Ser. No. 672,916, April 2, 1976, Pat. No. 4,007,010, and a continuation-in-part of Ser. No. 485,548, July 3, 1974, abandoned.

[51] Int. Cl.² .................. G01N 27/00; G01N 31/00; G01N 33/00
[52] U.S. Cl. ........................ 23/253 TP; 23/253 R; 23/259
[58] Field of Search .......... 23/253 TP, 230 R, 230 G, 23/259, 253 R; 206/219; 116/114 AJ

[56] References Cited

U.S. PATENT DOCUMENTS

| | | | |
|---|---|---|---|
| 3,036,894 | 5/1962 | Forestiere | 23/253 TP X |
| 3,552,928 | 1/1971 | Fetter | 23/253 TP |
| 3,620,678 | 11/1971 | Gurgan et al. | 23/253 R |
| 3,689,224 | 9/1972 | Agneu et al. | 23/253 TP UX |
| 3,697,227 | 10/1972 | Goldstein et al. | 23/253 TP |
| 3,713,779 | 1/1973 | Sieago et al. | 23/253 TP X |
| 3,776,515 | 11/1969 | Johnson et al. | 23/230 R |
| 3,917,453 | 11/1975 | Milligan et al. | 23/253 TP |

*Primary Examiner*—Barry S. Richman
*Assistant Examiner*—Michael S. Marcus

*Attorney, Agent, or Firm*—Behr & Woodbridge

[57] ABSTRACT

Analytical test strip apparatus for chemical, physical and biological experiments on small samples of fluids or fluid-like materials, consists of a thin, flat, hollow, pliable strip the interior including a channel completely filled with a thin layer of an inert liquid, preferably of a grease like consistency, into which liquid is introduced a small amount of the fluid to be tested, to form a movable "blister". The blister is propelled through the inert liquid, which confines it at all times front and rear, by applied external pressure. A plurality of chemical, physical, biological or detection stations are typically located in said channel. A physical station might consist of a filter membrane; a chemical station of a small pocket of chemical reagent; a detecting station of a material sensitive to pH. The stations are confined by the inert liquid filling the interior channel of the strip. In addition to forming the front and rear walls of the movable blister, the inert liquid also prevents migration of reagent located in a station, excludes air and other matters and prevents escape of noxious material being analyzed. In operation, a small portion of fluid is introduced into the strip top and the top is pinched to form a bubble or blister therein. The pinch line is drawn down the strip length forcing the blister ahead of it. As the blister proceeds down the tube, it is subjected to chemical, physical, biological and detecting operations as it passes through the different stations. One side of the tube being preferably transparent, results of the operations may be visible to the eye.

19 Claims, 20 Drawing Figures

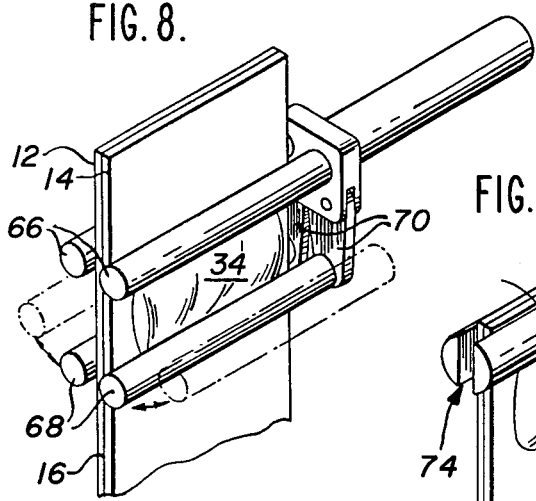
FIG. 8.
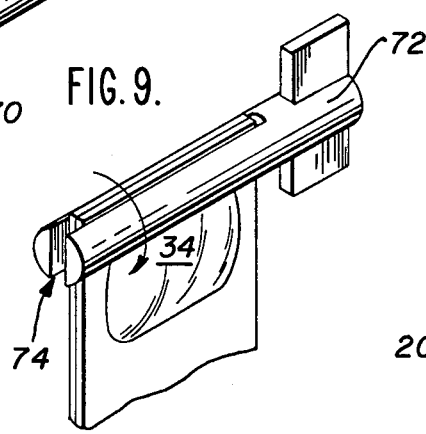
FIG. 9.
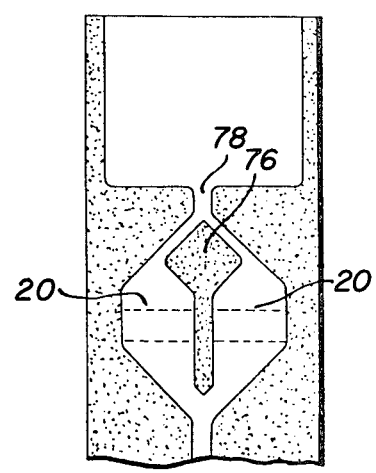
FIG. 10.
FIG. 11.
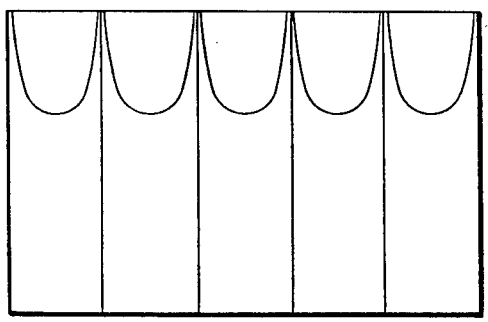
FIG. 12.
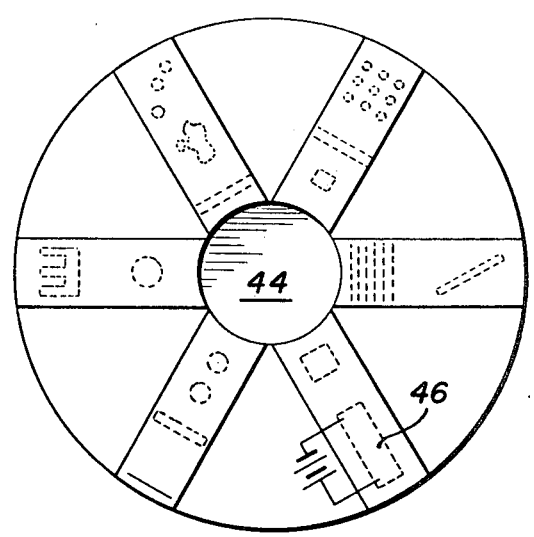
FIG. 13.
FIG. 14.
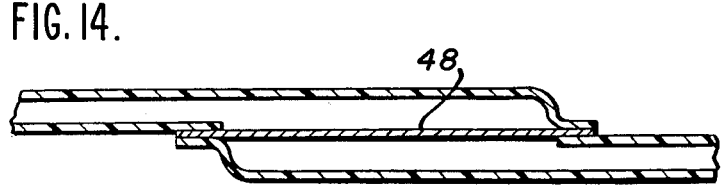
FIG. 15.
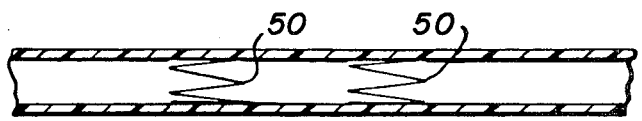

ANALYTICAL TEST STRIP APPARATUS

CROSS-REFERENCE TO RELATED APPLICATIONS

This application is a continuation-in-part of U.S. application Ser. No. 485,548 filed July 3, 1974, now abandoned, and of U.S. application Ser. No. 672,916 filed Apr. 2, 1976, now U.S. Pat. No. 4,007,010 issued Feb. 8, 1977, the entire disclosures of which are hereby incorporated by reference.

BACKGROUND OF THE INVENTION

1. Field of the Invention

This invention generally relates to an apparatus and method for performing a variety of chemical and physical operations upon a small sample of fluid or fluid-like material. In particular, the invention is directed to a thin, flat, hollow test strip the interior of which is filled with an inert liquid medium and which includes at least one physical, chemical, biological or detecting station wherein a blister of sample may be introduced into the top of said strip and positively propelled forwardly ahead of a pinch line through the inert liquid medium to each station.

2. Description of the Prior Art

In a typical continuous flow type analyzer samples of fluids to be analyzed are pumped sequentially through a long "pipe" or column and at various points along the pipe are subjected to specific chemical or physical processes. Often the individual samples are broken up by air bubbles in the pipe into small segments. Each segment receives the same treatment and at the end of the pipe the segments are typically comingled or enter another type of analyzer, for example, a colorimeter. In operation, different samples of materials to be analyzed are often separated one from another by a slug of water. Continuous flow analyzers of the type just described are produced by the Technicon Corporation and are well known to those of ordinary skill in the art. While such continuous flow analyzers can be very effective and do accomplish their desired goal, they do possess several drawbacks. Chief among the drawbacks encountered with such continuous flow type analyzers is that they are generally expensive, bulky in size, and non-disposable. Conversely, the subject of this invention is a flexible analytical type strip which will allow relatively complicated chemical processes to take place therein but which does not require sophisticated expertise to operate. Furthermore, the flexible analytical strip of this invention is much less expensive to produce and may be easily disposed of after use. Alternatively, however, it may be possible to re-charge the tube if so desired.

In general, the encapsulation of a reagent in plastic is not entirely new. For instance, part of the technique employed by the well known Polaroid Land Camera is to capture a chemical reagent in a plastic pouch and then, by applying roller pressure to it, force the pouch to rupture and spread its contents over a sheet of chemically treated paper for the purpose of developing the same. Also, the desalination of salt water has been accomplished in emergencies by introducing the sea water into a pouch containing a reactive silver containing substance and then squeezing the water out through a filtering medium into the mouth.

Prepackaged plastic analyzers are described in several recent United States patents, of which the following may be significant with respect to the instant invention: Johnson et al U.S. Pat. No. 3,476,515; Blackburn et al. U.S. Pat. No. 3,476,515; Johnston et al. U.S. Pat. No. 3,554,704; Schwartz U.S. Pat. No. 3,660,033; Agnew et al. U.S. Pat. No. 3,689,224; Goldstein et al. U.S. Pat. No. 3,697,227; Shapiro U.S. Pat. No. 3,713,780 and Nighohossian et al. U.S. Pat. No. 3,715,189. The foregoing can be broadly described as being plastic devices containing one or more reaction chambers into which certain chemical agents or samples may be added. In Johnson et al the agents are added by rupturing an internal depression filled with reagent. In Schwartz, the reagent or indicator is located in the reaction chamber itself. Guigan et al. U.S. Pat. No. 3,620,678; Fetter, U.S. Pat. No. 3,552,928 and Sirago et al. U.S. Pat. No. 3,713,779 are also indicative of prior art manipulative laboratory devices.

Of special interest is Forestiere, U.S. Pat. No. 3,036,894. The Forestiere patent discloses a "Method of Using Testing Containers" in which a linear chain of small, joined plastic reaction vessels, which are hollow chambers or pouches or bags containing predetermined amounts of reagents are connected together between two pieces of plastic material in strip form. A sample of material is introduced into the top hollow chamber and then squashed through the subsequent chambers in linear order by means of a pair of squeeze rollers. The reagents in the respective hollow chambers are separated one from another by an adhesive barrier "of relatively small area" which will break open when the matters in the chambers are squeezed strongly against it.

The present invention differs from the device disclosed in the Forestiere patent in several major respects. Most importantly, the present invention has nothing to do with hollow containers, chambers, pouches or bags. According to the Forestiere disclosure reactions are constrained to a pre-set, linear order. That is the sample, after being put in the top bag, is constrained to enter into the following chamber and react with the reagent there and then must enter into the next chamber, and so on in predetermined order. In the present invention the direction of blister travel can be changed according to the demands of the experiment. The device disclosed in U.S. Pat. No. 3,036,894 can be unsatisfactory in operation as may be seen from the following consideration. Upon crushing or squashing the entrance chamber the sample is squeezed into the first hollow reaction chamber and then reacts with the reagent therein. The entire contents of the first reaction chamber is then crushed into the second pouch to react with the reagent there. The combined contents of the first and second pouches are then squeezed into the third and so on. This may cause the adhesive barriers down the chain to expand open far in advance of the sample being squashed through the chain of chambers and cause the final chamber which is sealed at its end to distend and balloon. The effect may have to be mitigated by having compressible reagents or having the chambers largely filled with air. To prevent excessive ballooning appropriate venting mechanics would have to be provided. However, vents would largely militate against the processing of noxious material or virulent bacteria, viruses, etc. The device according to U.S. Pat. No. 3,036,894 involves not only chambers in a fixed linear array but also predetermined amounts of reagent in fixed positions with which to react the sample. In the present invention the reagents of interest may be in fixed position and be of predetermined amount but may also be in any position desired, even mobile of themselves and of any desired amount because in the present invention a blister may be not only of the material being tested but a second (or third, or fourth, etc.) blister may be a blister containing the reagent. Such a reagent blister may be pushed around, separated into portions, etc. at the will of the experimenter.

In none of the foregoing well known devices does the analysis appear to be performed in an apparatus or according to the method of the present invention. Among the chief differences is the fact that, due to the unique construction of the present invention, it is possible to manipulate the "blister" of sample through a plurality of physical and chemical operation stations in a manner not previously described by the prior art. By keeping the sample in a discrete blister it is possible to perform the analysis with little loss of volume due to sidewall adhesion effects and with minimum mixing with atmospheric air. This allows for relatively precise volumetric analysis and a great deal of physical control over the sample. Also it is possible to overcome surface tension problems associated with small specimen sizes, therefore improving accuracy with smaller samples. In general, gravity has not been found to be satisfactory as a driving mechanism because it is not strong enough to overcome the resistance associated with inert liquid medium. However, the present invention also contemplates the use of apparatus and techniques to accomplish the propulsion of the discrete blister down a strip. Obviously, many more operations can be performed on a blister since it loses little of its volume as it is analyzed. In this respect, much more sophistocated analysis can be performed on the sample than would be previously done without the aid of very expensive equipment. It was in the context of such a need that the following apparatus and method was invented.

SUMMARY OF THE INVENTION

A hollow, flexible plastic strip is formed the interior of which is filled with a layer of an inert liquid medium and which includes one or more chemical, physical, biological or detecting process stations. The liquid to be analyzed is introduced into the top of the tube or strip and a pinch line is formed behind the sample thereby trapping the liquid at the top of the strip. The pinch line may be formed by either crimping the top and rolling it, using a doctor blade, or a pair of rollers, etc. The pinch line is then drawn down the length of the strip in such a fashion as to force the sample through the inert liquid medium and through the different operation stations. The inert liquid medium serves as the leading and trailing edge of the blister and along with the sidewalls gives it dimension. This is true whether the blister is moved "up" or "down" the strip. The inert liquid medium also serves to preserve the integrity and separate the stations and any reagents at those locations and also serves to exclude air and other matters from the sample being analyzed and prevents noxious matters in the sample from escaping. Preferably, at least one side of the tube is flexible and at least one side is transparent or translucent so that the effect of the chemical reagents at the operation stations may be observed.

These and other objects and advantages of the present invention will be more fully understood upon a reading of the following specification taken in view of the attached drawings.

BRIEF DESCRIPTION OF THE DRAWINGS

FIG. 8 is a perspective view of a roller device which may be used to propell a blister down a strip while preventing the channeling of the sample as it progresses downwardly;

FIG. 9 is a perspective view of a key-like device that may be used to propel a blister of sample down the test strip;

FIG. 10 is a front elevation of another embodiment of the present invention in which the stream of fluid is divided in two, separately processed and subsequently comingled;

FIG. 11 is an elevated view of a plurality of test strips connected together in parallel fashion;

FIG. 12 is a view of another embodiment in which a plurality of test strips are assembled in a star-shaped configuration;

FIG. 13 is a cross-sectional view of another analytical tube of the present invention in which the pocket for receiving the fluid is formed by a pair of overlapping, flexible sheets in which one sheet is shorter than the other;

FIG. 14 is a cross-sectional view of a strip according to the present invention in which a filter membrane is stretched across the overlapping center section of the flat layers of the strip;

FIG. 15 is a cross-sectional view of another embodiment in which the filter sections are expandable and form zig-zag shaped pockets in the strip itself;

DETAILED DESCRIPTION OF THE INVENTION

In the course of this description it will be understood that like numbers refer to like elements in the various different embodiments.

Figure 1:
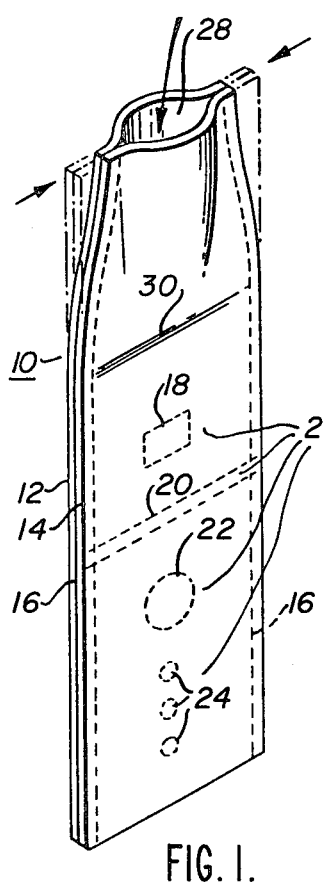
FIG. 1 is an elevated view of a flexible analytical strip according to this invention prior to the introduction of a fluid to be analyzed into the top thereof.
Figure 2:
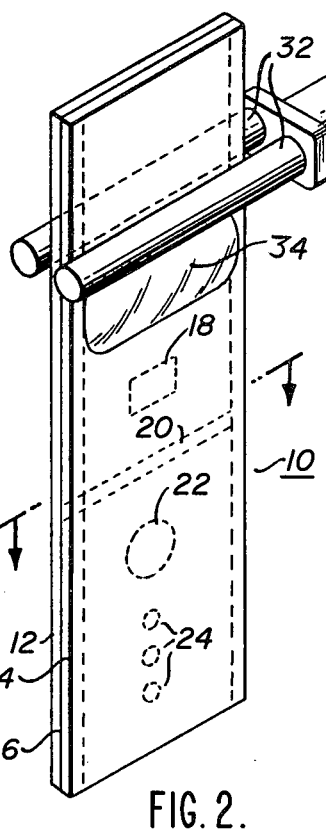
FIG. 2 is a view of the tube of FIG. 1 in which a fluid to be analyzed has been introduced into the strip and a pinch line has been formed in the strip thereby creating a blister of fluid at the top.
Figure 3:
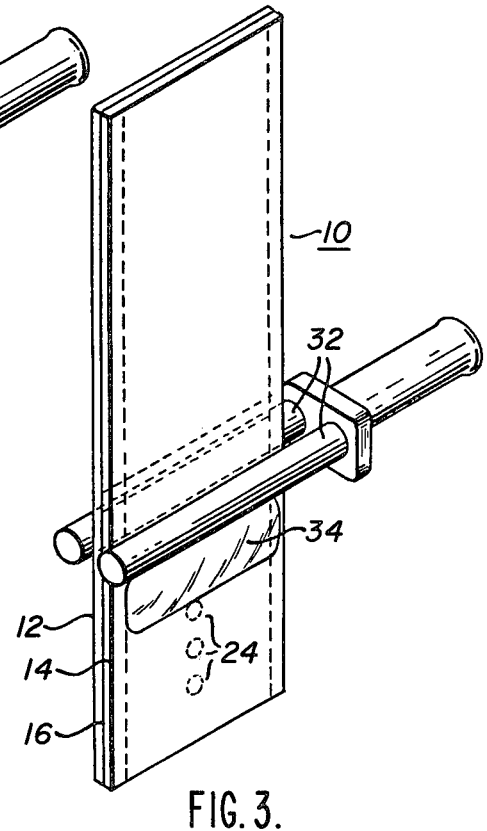
FIG. 3 is another view of the blister shown in FIG. 2 as it proceeds past the chemical, physical and analytical operation stations.
Figure 4:
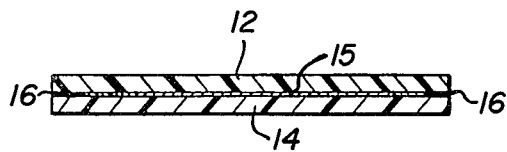
FIG. 4 is a cross-sectional view of an embodiment of the present invention in which the test strip is made from two separate pieces of plastic connected together at the edges by a heat seal or a permanent adhesive.
Figure 5:
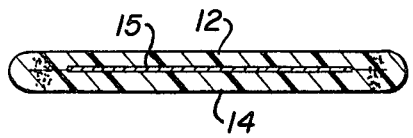
FIG. 5 is a cross-sectional view of an embodiment of the present invention in which the test strip comprises a flattened plastic tube.

An example of the flexible analytical strip according to a preferred embodiment of the invention is illustrated in FIGS. 1, 2 and 3. The body of the flexible analytical strip 10 is shown in FIG. 1 to include a back layer of flexible material 12 and a front layer of flexible material 14. Preferably, front and back layers 12 and 14 are made of plastic and at least one of the layers consists of, at least partially, a translucent or a transparent material. A pair of side seams 16 serve to fasten the front and back layers one to another in such a fashion as to form a collapsed hollow tube or strip with a channel therein. With plastic materials such as polyethylene, polystyrene, polyvinyl acetate, it is relatively easy to make such side seams 16 from heat seals; however, it is possible that other methods may be just as satisfactory. A side view of this embodiment is seen in FIG. 4. According to an alternative embodiment, it is also possible to make the flexible analytical strip 10 from a straight piece of polyethylene tubing which has been flattened in the manner illustrated in FIG. 5. The analytical strip according to FIGS. 1, 2 and 3 includes a plurality of operation stations 18, 20, 22 and 24 within its internal channel. Each of the stations 18, 20 22 and 24 are referred to as operation stations 26. It is to be understood that the operation performed at stations 26 may be either physical or chemical in nature. According to the embodiment shown in FIG. 1, stations 18 and 22 include chemical reagents which react chemically with substances mixed therewith. On the other hand, station 20 is a physical operation station. According to this preferred embodiment, a filtration station performs a physical filtering operation on the substance passing through the strip. Station 24 is a detection station in which the results of the operations in the analytical strip can be observed. The interior of the flat, hollow strip is completely filled by the inert liquid medium 15, a gel or grease-like substance, such as petroleum jelly which entirely engulfs the stations and acts as the leading and trailing edge of the blister irrespective of its forward or backward motion and so delimits the blister as to volume. The inert liquid medium also serves to confine any reagent at a station location excludes air and other matters from the system and prevents the escape of noxious substances. The inert liquid medium preferably has a consistency such that the blister in the system is held at one position until the blister is caused to move by a suitably directional force applied external to the strip.

It should be understood by those skilled in the art that the inert liquid medium 15 includes those materials, and indeed it is preferred to use those material which have high viscosity and which might be considered to have pseudosolid status such as gels, greases, pressure sensitive adhesive agents and soft waxes. It should be understood that no limitation of actual viscosity is considered to be critical to this invention since the actual viscosity will vary in accordance with the material utilized and the temperature at which the reactions contemplated are carried out. Having a view therefore, to the foregoing conditions that the inert liquid medium 15 and the fluid in the blister shall be inert and imiscible with reference to each other, suitable inert liquids include liquids having a hydrocarbon skeleton which may be cyclic or acyclic, aromatic or aliphatic. These materials may, if desired, contain as substituents, substantially reactive groups such as oxygenated groups, for example, hydroxy, keto, hydrocarboxy (acid), alkanoyl carboxy or aroylcarboxy (ester), halo, and the like as well as substantially inert groups for example, oxo, alkyl, aryl, or aralkyl.

Also included in this general organic category are perhalogenated liquids and silicones. In the case of the silicones the substituent groups utilized may be similar to those above.

Also included as suitable inert liquid medium 15 for more specialized purposes, particularly where it is desired to operate at slightly elevated temperatures, are liquid or low melting metals such as mercury, or low melting alloys such as Woods metal, liquid metaloids, and liquid sulfur, as well as liquid salts.

It will be recognized by those skilled in the art that use of these somewhat more exotic liquid media may require the use of special temperature conditions as well as the use of special temperature resistant materials which form the pliable layer under which the reactions of the present invention are to be carried out. Clearly, the material of the pliable layer must be temperature stable at the desired temperature and chemically inert with respect to the agents constituting the liquid medium.

In addition to the liquids set forth above, gels, greases, pressure sensitive adhesive agents, and waxes of more complex chemical constitution may be utilized provided that they meet with the aforementioned basic criteria of inertness and imiscibility with respect to the fluid in which the reaction is to take place. Also, included as a suitable liquid medium is water and water containing materials dissolved therein.

At the top of the tube is a sample insertion pocket 28 which may be formed by drawing side seams 16 toward one another in such a fashion as to cause the two layers 12 and 14 to pucker and form a small opening therebetween.

Into this pocket may be introduced, for example, a fluid sample to be analyzed or processed. It is anticipated that an invention of this sort will have applications in the medical analytical field and, therefore, substances such as blood and urine may typically be analyzed. The bottom of pocket 28 is defined by a line 30 where the inert liquid medium begins.

The following is a detailed description of the operation of the invention according to typical preferred embodiment. Initially a sample of fluid to be analyzed is placed in pocket 28 and the rollers then pinch the top of the pocket thereby forming a blister 34 therein. As the rollers 32 move downwardly the inert liquid medium opens to permit the passage of the blister and closes behind after the blister's passage. The blister 34 first encounters station 18 consisting of a deposit of reactive liquid reagent with which the contents of blister 34 are caused to unite. At that point, a chemical reaction takes place and this, therefore, represents the first step of a chemical and analytical process. Further downward movement of the rollers 32 cause the blister 34 to advance through physical operation station 20 where it is filtered. As the fluid portion of the blister 34 is forced through the filtration medium of station 20, it might leave behind solid materials, for example, precipitates. As rollers 32 continue to move downwardly, the fluid passes from filtration station 20 and into a second reagent station 22. At that point, according to the illustration, another chemical reaction takes place. Finally, as blister 34 continues to advance toward the end of the tube 10 under the influence of rollers 32, it encounters detection station 24 at which point there are illustrated a plurality of dots 24 which may be sensitive to a variety of different selected reagent conditions. For instance, detection dots 24 may be sensitive to pH or any other characteristics which is important. It should be understood that, according to the preferred embodiment, at least one side of the strip 10 is partically of wholly translucent or transparent.

The fluid constituting the blister which will either be, per se, the subject of reaction in the system of the present invention or will act as a carrier therefor may be either in the liquid or gaseous state.

It will be understood by those skilled in the art that the fluid to be analyzed must be substantially compatible with respect to the aforesaid inert liquid medium. That is to say that it will not react chemically with said medium, or be physically effected thereby such as dissolving therein. It should of course, be understood that these criteria of chemical and physical inertness cannot be considered as absolute. Nevertheless, the degree of interaction shall be sufficiently low as to cause no significant variation in the phenomena to be measured or the reactions to be carried out in the system as a whole.

Thus, for example, where petroleum jelly is the inert liquid, the reactions contemplated may be carried out on aqueous fluids or strongly polar oxygenated organic solvents such as alkanols, or alkanoic acids. On the other hand, substantially non-polar organics such as hexane or benzene or halogenated organics such as chloroform, methylene chloride or the like would not be suitable since they tend to dissolve the jelly. It is also inadvisable to utilize the fluids which tend to have a surfactant action on the liquid medium. That is to say that part of the chemical constituent of the fluid would tend to dissolve in the sealant liquid. Further, care must be taken to avoid emulsification which may sometimes tend to occur when the reactions are carried out on strongly alkaline medium using a substantially inert organic liquid such as petroleum jelly.

It will of course be understood by those skilled in the art that where, for example, aqueous media are employed as the sealant liquid, the working fluid constituting the blister should be similarly inert with respect thereto. Thus, the working fluid may be an organic liquid such as hexane, but not an organic liquid such as an alkanol for example ethanol; a gas for example, air, oxygen, or nitrogen, but not a gas such as chlorine or sulfur dioxide, a metal such as for example, mercury, but not a metal such as sodium or potassium.

Those skilled in the art will recognize that certain liquid/working fluid combinations will constitute borderline cases with respect to compatibility, but the existence of such borderline cases does not in any way detract from the general applicability of the method.

It is anticipated that, in most instances, a specific predetermined volume of solution to be analyzed will be inserted in the pocket; however, it is not necessary that the precise volume be known in many instances. While a pair of rollers 32 are illustrated as forming the seal at the trailing edge of bubble or blister 34, it should be understood that a wide variety of devices are also suitable for performing the same operation. For instance, it is possible to use a "doctor knife" or "doctor blade" or similar sort of mechanism for sealing the bubble. See, for example, element 42 in FIG. 7. Also, it is conceivable that a pad or pillow could be used to perform the same function. Another blister propelling mechanism would be to roll the strip tightly upon itself. This technique will be discussed in more detail later with respect to FIG. 9.

According to the preferred embodiments, the mechanism used for forming the trailing edge of blister 34 is the pair of rollers 32. By drawing the two rollers 34 downwardly, the trapped liquid blister is caused to move ahead of the nip or pinch line formed between the rollers. The advancing blister parts the liquid medium 15 as it moves from station to station. The liquid medium 15 reseals behind the blister after its passage. The operation may be observed through the transparent walls of the strip and the results recorded.

Figure 6:
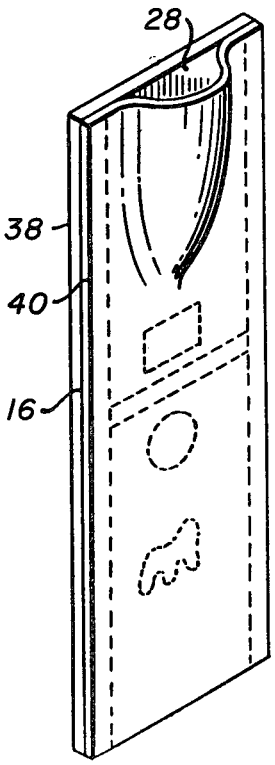
FIG. 6 is an elevation of another strip according to the present invention in which one side of the strip is relatively rigid and the other side of the strip is relatively flexible so that the blister forms on only one side of the tube.
Figure 7:
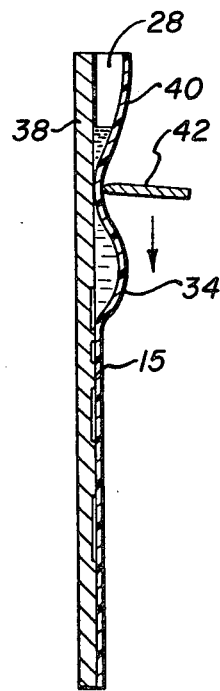
FIG. 7 is a cross-sectional view of the tube of FIG. 6 wherein a blister is propelled downwardly by a doctor blade.

Another embodiment of the present invention is illustrated in FIGS. 6 and 7 in which the bottom layer 38 is composed of a rigid plastic material and the top layer 40 is composed of a flexible layer. Bottom layer 38 and top layer 40 are again connected by a pair of side seams 16 which may preferably be heat-sealed in the case of plastic layers. In this embodiment, the pocket 28 is formed entirely in top layer 40 and the bottom layer 38 is not subjected to any substantial deformation during the blister forming and analysis process. In other words, the blister 34 is formed entirely in the upper layer 40. The basic operation of the blister test strip of FIGS. 6 and 7 is substantially the same as that shown for FIGS. 1, 2 and 3, except that FIGS. 6 and 7 illustrate the use of a doctor blade 42 which may be used interchangeably in place of the set of rollers 32 shown in FIGS. 1, 2 and 3.

As previously discussed, several types of blister propelling means may be used in conjunction with this invention. The use of pinch rollers 32 was disclosed in FIGS. 1-3. The doctor blade or knife technique was illustrated in FIG. 7. FIGS. 8 and 9 disclose two more types of propelling means. FIG. 8 discloses a pinch roller apparatus including a pair of front rollers 68. The rear rollers 66 serve the same purpose as rollers 32 in FIGS. 1-3, namely, they form a travelling seal behind the blister 34 and force the advancing blister ahead. The front rollers 68 serve the purpose of keeping the sample blister 34 confined between rollers 68 and 66. This is often desirable if the blister shows a tendency to loose its shape integrity. If there are no front rollers 68, the sample might have a tendency to "channel", that is, the leading edge of the sample blister may run between weak portions in the inert liquid medium in advance of the bulk of sample blister. The front rollers 68 are mounted on a pair of spring loaded pivotally mounted arms 70. In operation, the back rollers 66 are brought into position in the manner described with reference to rollers 32 of FIGS. 1-3. The front rollers are then swung into position in the manner described with reference to rollers 32 of FIGS. 1-3. The front rollers are then swung into position forming a traveling seal ahead of the blister 34. In this manner, the rollers 66 and 68 will bracket the blister and keep it as a relatively tight and uniform mass during analysis. Alternatively, channelling may be prevented by using transverse "semi-seals" of a stronger liquid medium which has a higher bonding strength than the normal liquid medium 15. As the blister moves downwardly, these "semi-seals" force the fluid to back up until the force of the rollers is sufficient to open the additional seal made by the stronger liquid. In this fashion, the fluid backs up behind the "semi-seal" until the internal pressure within the blister causes the "semi-seal" to open and permits the fluid to flow downwardly again. The "semi-seal" liquid medium is preferably used in conjunction with the normal liquid medium 15.

Another novel blister propelling means is illustrated in FIG. 9. The device consists essentially of a key 72 having a slot 74 therein. In shape, the key resembles a coffee can key or the type of key sometimes used to squeeze the paste out of toothpaste tubes. In operation, the top of the strip 10 is inserted into slot 74. The slot is narrower than the width of the strip so that a tight seal is formed behind blister 34. The key 72 is then rotated so as to roll the strip around the key. Since the strip is tightly wound around the key and the blister is forced ahead of the advancing roll, the rolled up strip serves as the propelling means. Unfortunately, this technique has the disadvantage that the effectiveness of the travelling seal is dependent upon the tightness of the roller strip and, for that reason, this method may be less desirable than the techniques previously described.

An apparatus and method for dividing a sample blister into two or more smaller sample blisters is shown in FIG. 10. This embodiment includes a divider island 76 located opposite the mouth of port 78. As the sample blister is caused to move down the tube, it passes through port 78 and impinges upon the spear-shaped head of divider island 76. At that point the blister is split into two parts which may be separately analyzed or treated. FIG. 10 illustrates a situation wherein the two smaller blisters are filtered at filter station 20 and later recombined. However, one sub-blister could be chemically treated and the other side physically treated, or one side could be treated and the other side not, etc. It is also not necessary that the treated blister recombine. Furthermore, each sub-blister could be further subdivided forming even smaller blisters if desired.

When it is necessary to perform a plurality of chemical analyses on the same solution or substance, it may be desirable to combine the analytical strips in the fashion shown in FIGS. 11 and 12. FIG. 11 illustrates an embodiment in which a plurality of analytical tubes are connected in side-by-side fashion so as to facilitate the simultaneous performance of a variety of different chemical and physical processes upon the sample. Alternatively, the test strips may be assembled in a star-shaped configuration as shown in FIG. 12 wherein they all share a common pocket 44. When the analytical tubes are arranged in the star-shaped configuration of FIG. 12, it may be desirable to elevate the pocket ends 28 of the strips above the bottom ends of the strips so that fluid in the central pocket will flow downwardly into each tube. Alternatively, of course, the tubes may lay flat. Of particular interest in FIG. 12 is the illustrated use of a physical process station 46 in which the sample blister is subjected to the influence of an electrical current or voltage. It should be understood during the course of this disclosure that the term "physical process" or "physical operation" also comprehends a variety of other operations such as electrical, etc. Another method of elevating tubes 10 when formed in a star-shaped pattern as shown in FIG. 12 is to angle the top of the tube as shown in FIG. 13. In this fashion, the bottom and top layers are separated and slightly elevated above the plane of the lower half of the tube so as to hold the liquid to be processed.

In the foregoing embodiments, the physical operation filter station has been described as a simple filter membrane sandwiched between the front and back layers of the test strip. However, due to space limitations within the strip, such a narrow filter may not present sufficient surface area to be effective. The embodiments shown in FIGS. 14 and 15 disclose techniques for increasing the effective area of the filter. According to the embodiment of FIG. 14, the filter 48 spans the juncture of two strips that are offset by one strip width from each other. Due to its simplified three-part construction, such a filter station would be relatively easy to duplicate. In FIG. 15, the filtration station 50 is formed from expandable V or Z-shaped zig-zag sections which unfold as the sample passes through them.

Figure 16:
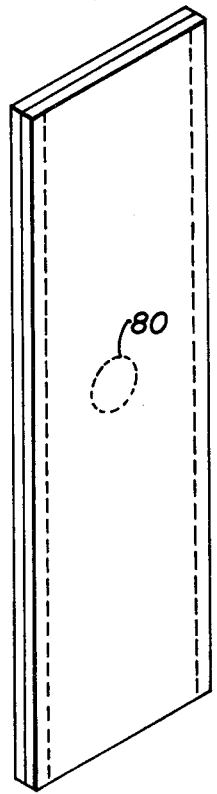
FIG. 16 is an elevated perspective view of an analytical strip including just one chemical process station.
Figure 17:
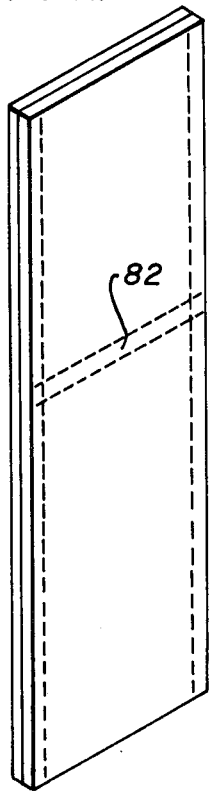
FIG. 17 is an elevated perspective view of an analytical strip including just one physical process station.
Figure 18:
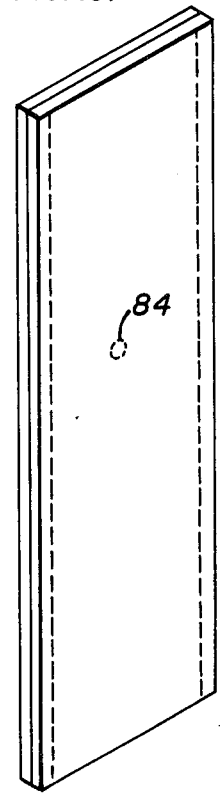
FIG. 18 is an elevated perspective view of an analytical strip including just one detecting process station.
Figure 19:
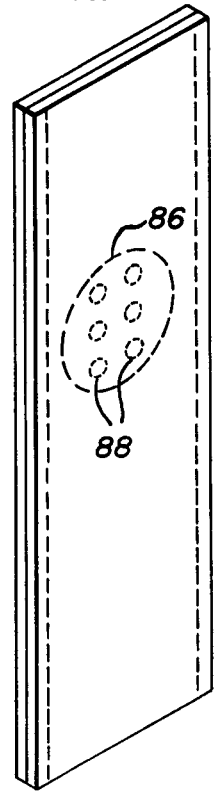
FIG. 19 is an elevated perspective view of an analytical strip including a detecting process station that comprises a plurality of detecting dots.
Figure 20:
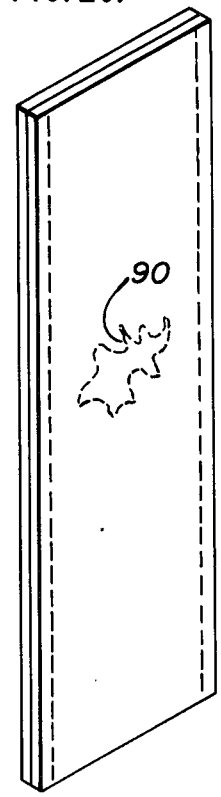
FIG. 20 is an elevated perspective view of an analytical strip including just one biological process station.

FIGS. 16 – 20 illustrate the fact that the present invention comprehends one process station as well as a plurality of process stations. FIG. 16 illustrates an analytical strip 10 including one chemical process station 80 similar to element 22 in FIGS. 1 and 2. Likewise, FIG. 17 illustrates one physical process station 82 similar to element 20 of FIGS. 1 and 2. FIGS. 18 and 19 illustrate detecting process stations. In FIG. 18 one detecting process station 84 is illustrated. In FIG. 19 the single detecting process station 86 comprises a plurality of detecting dots 88. FIG. 20 illustrates an analytical strip including one biological process station 90. It will be appreciated by those of ordinary skill in the art that the invention may comprehend just one chemical or physical or detecting or biological station. Alternatively, the scope of the invention also comprehends a combination of two or more chemical, physical, detecting or biological stations depending upon the requirements of the analysis to be performed. For example, a strip might contain one physical operation station and one detecting station, or one chemical station and a detecting station, or one biological process station and one detecting station, or one chemical and one physical process station, or one chemical and one physical and one detecting station. Or the strip could comprehend two or three chemical process stations and one physical station and one detecting station or any combination of chemical, physical, detecting and biological stations, etc. Additionally, the order of the stations in the analytical process is variable according to the demands of the analysis. It may be desirable, for example, to begin with a detecting station then go to physical, chemical, biological and other detecting stations respectively.

Further variations are also possible within the scope of the invention, as disclosed in FIGS. 1 – 20. One variation would be to have the chemical reagent deposited in indentations rather than on the surface between the top and bottom layers. Additionally, the physical operation station, such as the filtration stations, could be formed in an indentation rather than on the surface.

After the blister has passed to the bottom of the flexible tube, it may be desirable to either throw the strip and the solution away, if the experiment has ended, or, alternatively, it may be desirable to force the fluid out of the bottom for further experimentation of the sort that is not possible within the confines of the strip itself. For instance, the strip may be so constructed as to permit the removal of the solution by, for example, squeezing it out of the bottom of the strip in which case, the final detection station, such as that illustrated as element 24, may be omitted. In such a situation, the processed liquid sample may be subjected to further processing or analysis, for instance, as by a pH meter or in a retractometer, etc.

In some situations, it may also be desirable to dilute the fluid as it passes down the flexible, hollow strip. This could, of course, be done by adding a reagent station which consists of a bleb or vesicle containing an appropriate amount of inert fluid which would serve to dilute the sample blister when co-joined with it. It may also be desirable to cause the blister to be mixed or thoroughly dissolved within itself. This mixing could take place in a variety of different mixing stations. One mixing station, for instance, could consist of a reagent station which is subjected to vibration from the outside, for instance, from sonic or ultrasonic stimulation. Alternatively, mixing could take place in a mixing area of the strip where the blister encounters a plurality of baffles which would cause mixing to take place. Similarly, it would be possible to make a mixing station which consisted of an area with an appropriate configuration so as to cause a swirl or vortex pattern which by its own sheer forces could produce the mixing action.

One conspicuous advantage of the flexible analytical strip of the present invention is that it is relatively inexpensive and, therefore, may be disposed of after the experiment or analysis is performed. However, under certain circumstances, it may not be desirable to dispose of the fluid in the strip, and therefore, it might be advantageous to recycle the strip and renew the reagents therein. One method of renewing the reagents used would be to extend a hypodermic needle into the previously used reagent station and refill the same with a new reagent. In this fashion, a new experiment could be performed or the same one could be repeated, depending upon the nature of the reagent reintroduced into the operating station.

According to another method, it may be possible, by the selective and careful use of rollers and doctor blades, to cause the blister to reverse direction and retraverse its original path. Or the flexible tube may be used in a continuous mode of operation in which blister after blister would follow down the flexible tube after fresh reagents were reintroduced thereinto by the hypodermic method previously described. Additionally, fresh filters and the like may be introduced into filtration stations.

It may also be desirable to include in the test strip a detection station comprising a relatively clear plastic window through which light will readily pass. Such a station could be used in conjunction with a colorimeter or similar instrument for nondestructively testing the liquid sample from outside the strip. It will also be appreciated that the terms "top" and "bottom" or "terminating end" as used with reference to the strip are used for convenience of expression only and are not meant to imply that the strip has a particular operating orientation. As a matter of fact, the strip can be used in almost any orientation if external, non-gravity propelling means are used.

The stations have been preferably described as being locations at which physical, chemical and detection functions take place. However, it may also be desirable to include within the strip channel one or more biological stations such as shown in FIG. 20. Such a biological station might contain, for example, an antibiotic. Biological samples could then be introduced into the strip in the manner previously described and the effect of antibiotic reagents can be observed within the sterile environment of the strip. The strip can lend itself nicely to biological experiments since the blister forms a traveling air lock around the biological sample. In this fashion, contamination of the sample and of the biological reagents is greatly reduced in comparison to other, better known techniques.

It will be appreciated that the above described invention solves many problems heretofore not solved by the prior art. In particular, it provides an economical and simple means for performing chemical experiments and analyses on small amounts of fluids. It would also be a convenient size, typically two to twelve inches in length, and relatively easy to manufacture. The size of the sample blister can also vary considerably. In practice, it might range in size from the magnitude of a pinhead to the dimensions of an American quarter or larger. The proportions of the blister and the test strip are only limited by the size of the fluid sample anticipated. The dimensions suggested above are for purposes of illustration only and are not the ultimate limits of the invention parameters.

During the course of this disclosure the term station has been used to designate the location where the aforedescribed physical, chemical, biological or detecting activities take place. Within the context of this invention the terms "station", "operating station" and "process station" have been used interchangeably, however, the generic term "station" is preferred. In a similar manner the terms "detection station" and "detecting station" have been used interchangeably.

The invention can be further understood with reference to the following examples:

EXAMPLE I

The Preparation of a Test Strip According to the Preferred Embodiment of the Present Invention as Illustrated in FIGS. 1 through 3

The following describes a preferred embodiment of the present invention as shown in FIGS. 1 – 3 and its use. It also illustrates the manner in which a solid specimen may be analyzed. The example is one involving the analysis of flakes of old, white interior house paint for the presence of lead occasionally containing small amounts of copper.

The analytical test strip was prepared in the following manner. A sheet of polyethylene film 0.001 inch thick and measuring 9 inches vertically × 7 inches wide was placed on a flat surface. The various stations (shown collectively as element 26 in FIGS. 1, 2 and 3) were then located along the vertical center line.

At the bottom of the three detecting stations collectively noted as 24, and at a distance of ¾ inch from the bottom was placed a ¼ inch diameter disc of filter paper previously soaked in a strong solution of potassium ferrocyanide, $K_4Fe(CN)_6$ and dried. This was fixed in position using a very small amount of polystyrene-based cement.

In the same manner a similar disc of filter paper which had been soaked in potassium dichromate and dried was cemented in the center position of the three detecting stations. The center detecting station was located 1½ inches from the bottom.

The top or third detecting station, located 2¼ inches from the bottom, comprised a ¼ inch disc of filter paper which was cemented in location and which had been previously soaked in a solution of sodium sulfide and dried.

At chemical station location 22, located 4 inches from the bottom, a thin film of styrene cement was laid down and before it was dried was liberally sprinkled with zinc metal filings.

Physical station location 20, located 5½ inches from the bottom, comprised a fine filament of polyethylene, cemented cross-wise about 2 inches long. This was scored many times cross-wise using a sharp razor. Care was taken not to cut into the underlying plastic film. This scored barrier served as a filter.

Top chemical station location 18, positioned 6½ inches from the bottom was left empty as it was to receive the sample material which was to undergo its first chemical reaction.

On top of the entire assembly just described was placed a second clear polyethylene film of the same dimensions as the original base film. Welds were then run ¾ inch on each side of the center line using a bag sealer to yield a flat, edge sealed tube 1½ inches wide. The excess outer portions of the film were cut off. A light weld was made to the top of the filament at the physical station location 20.

Subsequently a ¼ gram portion of clear petroleum jelly was introduced into the top of the strip through opening 28. Using a doctor blade, and pressing down through the top film from the outside, the petroleum jelly was smeared throughout the length of the tube, completely filling it. Care was taken to eliminate all pockets, pits, etc., so that in effect the petroleum jelly filled the entire tube, enclosing and covering all stations and eliminating substantially all contaminating air from the environment. It is important to note that there were no chambers, pouches, bags, etc. of the sort common to other prior art devices. The foregoing thus constituted a preferred embodiment of the Analytical Test Strip apparatus.

The thus assembled test strip was then used to perform an analysis in the following manner. The top of the grease filled strip was opened down to position 18. This was easily done by inserting a knife blade (or it could even be a finger nail) and gently bowing the strip to form a mouth input port 28. At location 18 one or more flakes of the paint to be analyzed were inserted by means of tweezers and the strip then resealed by the grease. Generally a sample so positioned and sealed can be retained and stored in situ as long as desired.

At the beginning of the analysis the gel filled strip was opened again at the top and about 10 drops (about ½ c.c.) of 10% acetic acid was introduced about 2 inches deep into the strip. Using a suitable, flat blade and pressing from outside through the top film the bleb of acetic acid was worked down between the top and bottom layers of the strip and through the grease filled interior without entrapping any air. The grease filling closed behind the bleb and entirely surrounded it thereby forming an isolated sample blister.

Using a roller device the blister was moved down to the first chemical reaction station location 18, where the flakes of paint were located. As disclosed herein other types of propelling means such as a doctor blade could have been used instead. As the roller device proceeded downwardly, the grease filling always closed behind the sample therefore maintaining the integrity of the blister. At chemical reaction station location 18 a reaction took place between the acetic acid and the lead compounds in the paint, which were usually basic lead carbonate. The reaction caused the lead to dissolve and form a solution. It was found that the reaction could be facilitated by agitation from the outside by holding the point of a vibrator at location 18 or by including with the paint flakes some stainless steel filings which could be caused to vibrate by an external magnetic field and could be used if desired to heat the mixture by induction means.

After 20 minutes the blister of lead solution was moved down to the physical filter station 20 at which position the liquid was forced through the channels in the scored strip thereby leaving the larger particles behind.

The blister was then pushed further down and to the second chemical station location 22 where any copper in the solution precipitated out on the zinc filings. The zinc entering the solution does not interfere with subsequent steps.

The blister was then drawn to the first detection station. The station turned black indicating the formation of lead sulphide, which test showed that lead was present in the flake of house paint.

The blister was then drawn further to the middle detecting station. The middle detecting station also indicated the presence of lead by turning yellow due to the formation of lead dichromate.

The bottom station was used to detect whether or not the copper had been completely removed by the zinc at chemical station location 22. The station did not turn color. If copper still remained, the bottom station would have turned a brown color.

EXAMPLE II

Alternative Embodiment

A strip was prepared by placing a piece of transparent polyethylene film 0.001 inch thick and 8 inches × 6 inches down upon a diagram which served as a guide to side welds, station locations, etc. A first location was left blank. This was to serve as a physical and observation station location. At a location corresponding to element 20 in FIGS. 1 through 3 an indicator reagent station was prepared as follows: Across the strip was rapidly painted a line about 1 m.m. wide of polystyrene lacquer composed of polystyrene dissolved in acetone. Before the line was dry it was sprinkled with finely divided phenolphthalein. The polystyrene lacquer was allowed to completely dry and the excess phenolphthalein was blown away. Below station location 20 and in the area where stations 22 and 24 are indicated in FIGS. 1 through 3, five lines of polystyrene lacquer were painted. Before the five lines could dry they were dusted with finely divided sodium carbonate. These lines were then allowed to completely dry and the excess sodium carbonate was carefully removed. A second sheet of the same transparent polyethylene plastic was then laid over the bottom sheet. Using a hot wire type sealer the two pieces of plastic were sealed together with parallel seals approximately 1 inch apart and running lengthwise with the pieces. The excess plastic was then cut off at the sides. The seams thus formed were about 1/16 inch wide. The prepared stations were located between the seams in a manner similar to that illustrated in FIGS. 1 through 3. ¼ of a gram of white petroleum jelly was then introduced into the bottom of the flat tube thus formed. The tube was then laid on a rigid, flat surface. Very carefully, using a dull blade, petroleum jelly was squeezed the entire length of the tube by working from outside upon the top layer and gently pushing this way-and-that until the entire flat tube was completely filled from edge to edge, from top to bottom, covering all stations completely. Care was again taken to leave no trapped air, voids, cavities, etc. Excess petroleum jelly was squeezed out of each end. The result was a pliable, flexible, transparent strip totally enclosing all reagents in a solid film of petroleum jelly which measured approximately 0.0005 inch thick. It was found that a strip so constructed could be stored for many months, and was extemely rugged and very convenient.

The strip was used in the following manner. A sample of water from the effluent pond of a manufacturing plant was secured in a clean container. From this a few drops were drawn into a clean, glass medicine dropper whose open end had been drawn to a fine point. Using the fine point, a port into the grease filled strip was made by forcing the sharp point between the plastic films and parting the grease. Five drops of the water sample were introduced into the opening. Using a dull blade the droplet was worked away from the opening, the grease closing behind it so that the droplet was completely enclosed and not exposed to any contaminating environmental air. At this point the sample formed a very slight bulge in the assembly and this bulge is referred to herein as a "blister". The blister could be left sealed in such a position or could be processed immediately. To process, the strip was first laid down on a rigid, flat surface and then the blister was drawn down, that is to say caused to flow through, the grease thereby parting the grease layer which closed behind it. A doctor's blade was used to propell the blister from the outside to position 18 (see FIGS. 1 through 3) where it was examined using transverse light, for clarity, subsequently examined under an ultraviolet light for fluorescent traces of oil and then examined under a low power microscope. The blister was then propelled down to station location 20. At this position it was caused to vibrate by holding it against the modified end of an engraving pen of the sort used to mark metallic objects such as tools. At that point the blister sample picked up the phenolphthalein indicated. The sample did not change color, indicating that it was not alkaline. The blister was then drawn down to the first sodium carbonate station. At that point the blister was again subjected to agitation so that solution with the sodium carbonate could be accomplished. Sodium carbonate at this position was found to be insufficient to render the liquid in the blister a permanent red. In a similar fashion the motion of the blister was continued. Not until the blister had reacted with the sodium carbonate at the fourth sodium carbonate station was the liquid in the blister a permanent color. It had previously been ascertained that an effluent of such high acidity was undesirable.

EXAMPLE III

Multiple Detection Stations

In a manner similar to that described with reference to Example I and II, a strip like that of FIG. 19 was made of two films of copolymer of vinylidene chloride and vinyl chloride. As before, a position such as that indicated at 18 in the drawings was left free. At a position such as that indicated as element 22 in FIGS. 1 through 3 a series of five dots were placed across the strip in a side-to-side manner. The five dots respectively comprise different surface coatings known to be relatively resistant to water and each made opaque with finely divided titanium dioxide. These dots were then allowed to completely dry. A few drops of clean sea water were placed between the two plastic films of the flat tube. Using a dull, straight edge, the water was spread throughout the strip completely filling it, leaving no voids or cavities or entrapped air and completely enclosing the dots of surface coatings. The water acted in many ways as an adhesive and served as a liquid medium in the same fashion that petroleum jelly was employed in Example I and II.

Analytical test strips formed in the manner just described were used to test a wide variety of surface coatings against a variety of appropriate petroleum products. In one test a drop of SAE 20 motor oil was introduced into the end of the strip using a hypodermic needle. Using a doctor blade the blister containing the motor oil was drawn to the position corresponding to location 18 in the diagram, parting the water as it moved. The water closed behind the blister and resealed it as it progressed downward. At station location 18 the sample was examined with ultraviolet light. It fluoresced. This fluorescence of the sample was an indication of multi-ring aromatic compounds. Subsequently the blister of sample was moved further downwardly so that it covered the dots of surface coating where it was held for various periods of time at various incubation temperatures. After a period of time the blister was agitated and then drawn away from the detecting dots. Surface coatings whose dots washed off with the blister were considered to be unsuitable to serve as coatings for vessels which contained the SAE 20 motor oil under consideration where such vessels were liable to be contaminated with seat water.

The five dots of surface coatings were as follows, reading from left to right across the strip:
1. Linseed oil based coating.
2. Acrylic coating.
3. Furfural based coating, baked.
4. Silicone based coating.
5. Urathane based coating.

Upon incubation for a period of one year at 45° C it was found that the baked furfural based coating was most suitable, in this particular experiment.

EXAMPLE IV

Single Chemical Station

In a manner similar to that described with reference to Example I through III, a flat tube like that illustrated in FIG. 16 was formed but this time using 0.0005 inch thick polyester film. No stations were preformed inside the strip. ¼ gram of Dow Corning silicone stopcock grease was introduced into one end of the strip. Carefully, using a dull straight edge, and pressing and manipulating from the outside, the stopcock grease was spread in such a fashion as to completely fill the space between the two films. Care was taken to leave no entrapped air, voids or cavities. The layer of stopcock grease measured 0.0005 inch thick.

Using a fine hypodermic needle, a droplet of Benedict solution was introduced into one end. The droplet was then moved away from the needle using a dull straight edge. The entrapped droplet now comprised a blister. As the blister was moved downwardly the grease parted but resealed behind the moving blister. So sealed, the test strip constructed in such a manner was portable.

A droplet of a test sample of urine was then introduced into the other end of the strip forming a blister therein. The blister was then moved down to mix with the benedict solution using a roller. This end of the strip was subsequently immersed in boiling water for five minutes. At times it was desirable to clip a weight to this end to keep is submerged. After heating the blister was examined by transverse light. A precipitate indicated a reducing substance in the urine, presumably a sugar substance.

EXAMPLE V

Single Detection Station

A strip was prepared in the manner previously described. A 0.0001 inch polyethylene film served as the walls of the strip and petroleum jelly was employed as the inert liquid medium between the film walls. At the position corresponding to station location 84 in FIG. 18 a small amount of silver nitrate was deposited. Areas before and after this location were left clear. Again, at all times care was taken to prevent voids, cavities, air entrappment, etc.

A sample of steam condensate from a sea water still was gathered in a clean container. Using a medicine dropper with a fine point, a droplet of water was injected into the plastic-grease-plastic sandwich and drawn down to the station containing silver nitrate. Here it was allowed to stand. It was then agitated with a vibrator. Subsequently the blister was moved down from the silver nitrate area and its turbidity measured. The presence of turbidity indicated that chloride, ie. sea water, had gotten into the fresh water side of the still. The degree of turbidity was a measure of how serious the contamination was.

EXAMPLE VI

Multiple Chemical Stations

This experiment illustrated the use of the Analytical Test Strip Device for testing urine for reducing substances using benedict's solution.

The strip was prepared in the following manner. A flat strip of polyethylene film 2 inches wide, 6 inches long and 0.001 inch thick was placed on a flat surface. At the bottom end of the strip was placed the materials, which when dissolved in water would constitute Benedict's Solution. Beginning at a position 2 inches from the bottom a thin deposit of Canada Balsam dissolved in Xylene was laid down in a fine line running across the strip. This was allowed to become tacky at which time the following reagents in solid form were placed on the Canada Balsam which merely served to hold the reagents in place:

A. At a point a ½ inch from the left hand side of the strip was placed 0.0173 grams of copper sulfate, CP, crystals;

B. On the center line of the strip was placed 0.173 grams of sodium citrate; and, C. ½ inch from the right hand side of the strip was deposited 0.2 grams of sodium carbonate crystals.

Once it was determined that the reagent solids were firmly stuck to the Canada Balsam, the Canada Balsam was permitted to dry.

Over the strip, with the dots of the reagent, was placed a second strip identical to the first. Using a bag sealer, the long edges of the strips were welded together.

About ¼ of a gram of clear petroleum jelly was then placed in the top of the flat, hollow tube just formed. Using a doctor blade, and pressing through the top film from the outside, the petroleum jelly was smeared throughout the interior, so as to form a thin center layer. This coated the dots of the reagent completely. Care was taken to eliminate all voids, pockets, etc.

At the beginning of the analysis a mouth or port was formed at the top of the device. A knife blade was used to open the top of the tube and the opening was maintained by pushing the welded sides toward one another causing the walls to bow away from each other. A finger nail or a variety of other objects can be used to initiate the formation of the opening.

One c.c. of distilled water was then introduced into the top input port. A propelling means was then used to move the water downwardly to the reagent dots. It was noticed that the grease reformed or resealed the sandwich after the drops moved forward. The reagent drops dissolved in the water to form a blister of Benedict's Solution.

A drop of urine was then introduced into the device in a similar manner and moved down through the perpetually sealing, petroleum jelly liquid medium so that it joined with the Benedict's Solution. The strip, at least its lower end, was then immersed in boiling water for five minutes.

The test was positive for reducing substances in the urine as the solution in the blister became a redish color and there was a red-yellow precipitate.

EXAMPLE VII

Single Detection Station

An Analytical Test Strip was made from two pieces of transparent polyester film 6 inches × 2 inches with each being 0.0005 inches thick. These were cemented together at the longitudinal edges. The flat hollow tube so formed was then filled with a thin layer of clear petroleum jelly which served as the continuous liquid medium center filling of the sandwich. The foregoing was used in conjunction with a microscope and a reticle in an investigation of an industrial shop in which the air was heavy with fine silica particles.

At the beginning of the experiment, the air in the shop was drawn through 100 c.c. of water, in a 250 c.c. Erlenmeyer flask. After a period of time, the dust particles collected in the water trap were counted, as follows.

Ten drops of the dust bearing water were then introduced into the test strip by opening a port in one end. The water was then moved down into the tube a short distance through the petroleum jelly by acting from outside through the film using a suitable propelling device. The petroleum jelly resealed after the liquid blister passed through it thereby preserving the specimen as long as desired or at least until it was possible to finish the examination. For this reason the device serves as a very convenient and economical piece of field equipment.

Under the microscope with appropriate prior art techniques and using the reticle it was relatively easy to count the number of particles per unit volume of liquid. It was then possible to estimate the particle contamination of the industrial atmosphere by matching the number of particles against a previously developed calibration curve.

EXAMPLE VIII

Biological Station

This example illustrates the use of the device in ecological investigations for determining the suitability of various natural waters for sustaining aquatic life. The strip is similar to that illustrated in FIG. 20. Frequently waters contain toxic matters which might be harmful to aquatic life. The Analytical Test Strip was prepared from two pieces of polyethylene film, each 0.001 inch thick and measuring 6 inches × 2 inches. The bottom strip was first laid on a solid surface. Across its lower end 1 inch from the bottom was drawn a line ⅛ inch wide with egg white. Before the egg white completely dried it was liberally spinkled with infusoria powder, which may be obtained from many biological supply houses and consists of the encysted forms of many protozoans. The egg white, on drying served to maintain the powdered granules in position.

A second strip of polyethylene was then laid upon the thus prepared bottom film. The longitudinal edges were sealed using a bag sealer, to form a flat hollow tube.

Approximately ⅛ gram of clear petroleum jelly was then introduced into the top of the strip. The petroleum jelly was then squeezed and smeared throughout the length of the tube, completely covering the desposit of infusoria powder held in place by the egg white. The distribution of petroleum jelly was performed through the use of a doctor blade working from the outside and through the top layer of film.

The experiment was begun by opening an input port in the top end of the flat, grease filled strip with a thin blade. Three c.c's of the water to be tested were then introduced into the input port. The water was then squeezed down the tube by means of a suitable propelling means such as a roller system or doctor blade, until the blister engulfed the deposit of infusoria powder. The foregoing apparatus can be used to determine if the water is too toxic to support life. After one week at room temperature the water in the blister was alive with protozoan life which could be seen easily either by unaided visual observation or by microscopic observation, it can be assumed that the water was not too toxic to maintain life. On the other hand, if life had not been observed in the blister then the water would have contained toxic matters.

EXAMPLE IX

Single Detecting Station

This example demonstrates the present invention in a simple detecting test mode wherein the pH of a soil sample may be determined.

The strip employed in this example comprised a petroleum jelly filled, flat strip made of two pieces of 0.0005 inch thick strips 2 inches × 6 inches transparent polyvinyl chloride polyvinylidene chloride copolymer film with sealed edges. At a predetermined location, 1 inch from the bottom of the strip on the center line was fixed a ¼ inch circle of indicating paper whose color change indicates pH. The indicating paper was located inside of the strip entirely engulfed by the petroleum jelly.

The first step of the analysis was to place a heaping teaspoon of the soil to be tested in a 250 c.c. beaker with 50 c.c.'s of distilled water. After stirring and then permitting the solution to settle, about ½ of a c.c. of the top relatively clear liquid was withdrawn using a medicine dropper.

In the second step of the experiment the liquid was introduced into top of the strip. Using a doctor blade the liquid was moved down through the grease, which resealed behind it, to wet the indicator paper. The change in color of the paper indicated the pH of the sample. The test paper in an experiment on a soil sample from a local mossy woodland turned a dirty color (between an orange and a light green). This indicated a pH of about 6.0. The test paper used was "pHydrion Soil Test Paper", a product of Micro Essential Laboratory, Brooklyn, N.Y.

EXAMPLE X

Multiple Detecting Stations

This example illustrates the use of my device in a mode involving a plurality of read out indicator positions or detecting stations such as illustrated in FIG. 19.

The concept basic to this example is that the material in the movable blister is a participant in a physical action or chemical reaction which will not occur until the blister is moved into the area of the read out indicator positions. Each indicator position has a differing composition or structure so that each one will perform in a known graded manner involving time or temperature or similar observable parameter. In other words, the presence of the fluid in the blister in the activity area permits something to happen which otherwise could not happen.

The strip according to this example is constructed in the manner previously described from two thin plastic films and includes a very thin center filling of an inert grease-like liquid medium such as petroleum jelly.

A blister of the fluid sample may be positioned in the upper portion of the strip and completely sealed in by the top and bottom films and surrounding grease. Thus prepared the blister is ready to be moved downwardly by a propelling mechanism such as rollers, doctor blades, etc. The detecting reagent deposits or structures are located at the other end of the strip on its interior and are completely surrounded by the inert liquid medium.

A strip thus formed can be used to determine solubility and solubility relationships in the following manner. A test strip was assembled using two strips of transparent polyester film each 6 inches × 2 inches and each 0.0005 inch thick. The bottom strip was laid flat on a smooth hard surface. Then a 2 × 3 matrix of six drops of gum arabic containing sufficient titanium dioxide to whiten it were laid down approximately 1 inch from the bottom. The 2 × 3 matrix was chosen merely for convenience sake. A circular or "clock" array could also have been used. Each drop was made thicker and larger than the preceeding one in a graduated manner. These dots were then allowed to dry. From the underside the dots appeared to be white. After the deposit had dried, the upper piece of film was laid on. The longitudinal edges were sealed and a thin filler of clear petroleum jelly was caused to completely fill up the interior of the strip thereby sealing the white gum arabic deposit. The petroleum jelly served as the inert liquid medium.

Approximately ½ c.c. of pure water colored deep black with highly dispersed carbon black was then introduced into the upper portions of the strip. Other colors may have been used but black has certain preferred visible advantages. The sample was drawn down into the strip, using a doctor blade, until it formed a completely sealed blister.

The experiment was begun by moving the black blister down the strip until it covered the white gum arabic deposits. This was done at room temperature of approximately 70° F. It was observed that the deposits then began to dissolve. The smallest deposit dissolved first, the next smallest deposit next, and so on. The progress of the experiment could be easily observed from the underside of the bottom strip as one by one the white dots disappeared and were supplanted by the black liquid in regular order according to the pre-determined time schedule.

In the next run, an identical Analytical Test Strip was prepared but this time instead of using pure water a 1% solution of gum arabic was used, again colored black as was the fluid in the blister. Following the same procedure, again at room temperature, the previous procedure was repeated, this time to give data pertaining to solubility rates of gum arabic in a 1% arabic solution.

A series of such runs was made with increasing solution strength until sufficient data had been collected so that useful curves could be drawn.

Other series of runs were made at ascending temperatures to determine the sensitivity of the dissolving rate to temperature. Similar runs were made at various pressures. Other runs were made using solutions of various chemicals to determine the solubility relationships of such solutions to gum arabic. The device has also been used on substances other than gum arabic. It has been found in general, that the device can be very useful in the field as well as in the laboratory or clinic.

In a general manner, while there have been disclosed effective and efficient emodiments of the invention, it should be well understood that the invention is not limited to such embodiments as there might be changes made in the arrangement, disposition and form of the parts without departing from the principle of the present invention as comprehended within the scope of the accompanying claims.

I claim:

1. An analytical test strip apparatus comprising:
   at least one substantially flat strip having a front layer and a back layer, said front and back layers defining a channel therebetween through which a sample of liquid may pass, said strip also including a sample input port and a terminating end, at least one of said layers being relatively pliable;
   a plurality of process station means linearly located in said channel; and,
   a thin layer of an inert liquid medium located in said channel, said liquid medium adhering said two layers to each other and being strong enough to prevent the forward movement of said sample in said channel solely under the influence of gravity but weak enough to allow said sample to linearly pass in a predetermined sequence through said plurality of station means in said channel under the influence of an exterior propelling means, said liquid medium so filling said channel as to constitute the medium through which the sample is propelled, the dimensions of said liquid medium being sufficiently broad so as to substantially exclude contaminating air from said station means.

2. An analytical test strip apparatus comprising:
   a substantially flat strip having a front layer and a back layer, said front and back layers defining a channel therebetween through which a fluid may pass, said strip also including a fluid input port and a terminating end, at least one of said layers being relatively pliable;
   a plurality of process stations linearly located within said channel and including at least one temperature detection station; and,
   a thin layer of an inert liquid medium located in said channel, said liquid medium adhering said front and back layers to each other and being strong enough to prevent the forward movement of said fluid in said channel solely under the influence of gravity but weak enough to allow said fluid to pass linearly through said channel under the influence of an exterior propelling means, said liquid medium so filling said channel as to constitute the medium through which the fluid is propelled.

3. An analytical test strip apparatus comprising:
   at least one substantially flat strip having a front layer and a back layer, said front and back layers defining a channel therebetween through which a sample of fluid may pass, said strip also including a sample input port and a terminating end, least one of said layers being partially translucent and at least one of said layers being relatively pliable;
   a plurality of process station means linearly located in said channel;
   a propelling means for linearly propelling said sample through said channel; and,
   a thin layer of an inert liquid medium located in said channel, said liquid medium adhering said two layers to each other and being strong enough to prevent the forward movement of said sample in said channel solely under the influence of gravity, but weak enough to allow said sample to pass through said channel under the influence of said propelling means, said liquid medium filling said channel so as to constitute the medium through which the sample is propelled and substantially excluding contaminating air from said station means,
   wherein said sample is introduced into said top sample input port and then linearly moved toward said terminating end through said liquid medium as an air-free mass by said propelling means thereby passing said sample in a predetermined sequence through said plurality of station means located in said channel.

4. The apparatus of claim 1 wherein at least one of said front and back layers is made substantially of a plastic-like material.

5. The apparatus of claim 1 wherein a plurality of said strips are connected in a side-by-side relationship.

6. The apparatus of claim 1 wherein a plurality of said strips are connected in a star-shaped pattern and have their sample input ports located near a common central point.

7. The apparatus of claim 1 wherein said propelling means is a doctor blade means.

8. The apparatus of claim 1 wherein said propelling means includes a key means which may be connected to one end of the strip and rolled in such a fashion as to propel the sample ahead of the roll.

9. The apparatus of claim 1 wherein said strip includes a divider means for dividing said channel into at least two separate channels, whereby said divider means serves to divide each sample into smaller samples suitable for subsequent processing.

10. The invention of claim 1 wherein one of said station means includes a filter station, said filter station comprising a flat piece of filter material located in the channel between two partially overlapping strips.

11. The apparatus of claim 1 wherein one of said station means includes a filter station, said filter station comprising a piece of expandable material blocking said channel in a zig-zag manner.

12. The invention of claim 12 wherein said strip includes at least one detection station comprising a clear plastic window through which optical instruments can analyze the properties of said sample.

13. The apparatus of claim 1 wherein said strip includes at least one biological station in which said sample reacts with a biological reagent.

14. The apparatus of claim 1 wherein said strip is formed from one piece of flattened plastic tubing.

15. The apparatus of claim 1 wherein said strip is formed from two separate layers of plastic joined together on their edges by a heat seal.

16. The apparatus of claim 1 wherein said propelling means comprises a first pair of rollers.

17. The apparatus of claim 14 wherein said propelling means further includes a second pair of rollers, said first pair of rollers serving to propel said sample, and said second pair of rollers serving to help contain the sample between said rollers.

18. The apparatus of claim 1 wherein one of said station means is a chemical station and another of said station means is a detection station.

19. The apparatus of claim 18 further including at least one physical station.

* * * * *